(12) United States Patent
Liolios et al.

(10) Patent No.: US 10,433,718 B2
(45) Date of Patent: Oct. 8, 2019

(54) EYE SAFE LASER ILLUMINATION IN OPHTHALMIC SURGERIES

(71) Applicants: Thomas Liolios, Los Gatos, CA (US); Michael Charles East, Farmington, UT (US)

(72) Inventors: Thomas Liolios, Los Gatos, CA (US); Michael Charles East, Farmington, UT (US)

(*) Notice: Subject to any disclaimer, the term of this patent is extended or adjusted under 35 U.S.C. 154(b) by 729 days.

(21) Appl. No.: 14/842,156

(22) Filed: Sep. 1, 2015

(65) Prior Publication Data

US 2015/0366443 A1  Dec. 24, 2015

Related U.S. Application Data

(63) Continuation of application No. PCT/US2014/030235, filed on Mar. 17, 2014.

(60) Provisional application No. 61/789,040, filed on Mar. 15, 2013.

(51) Int. Cl.
*A61B 1/06* (2006.01)
*A61F 9/008* (2006.01)
*A61B 3/00* (2006.01)
*A61B 90/30* (2016.01)
*A61F 9/007* (2006.01)

(52) U.S. Cl.
CPC ............ *A61B 1/063* (2013.01); *A61B 1/0638* (2013.01); *A61B 3/0008* (2013.01); *A61B 90/30* (2016.02); *A61F 9/00821* (2013.01); *A61B 2090/306* (2016.02); *A61B 2090/309* (2016.02); *A61F 9/007* (2013.01); *A61F 2009/00863* (2013.01)

(58) Field of Classification Search
CPC .......... A61B 1/06; A61B 1/063; A61B 1/0638
USPC ........................................... 351/221
See application file for complete search history.

(56) References Cited

U.S. PATENT DOCUMENTS

| | | | | |
|---|---|---|---|---|
| 5,508,760 A * | 4/1996 | Kobayashi | ........... | A61B 3/1225 351/205 |
| 5,892,569 A * | 4/1999 | Van de Velde | ......... | A61F 9/008 351/221 |
| 5,943,117 A * | 8/1999 | Van de Velde | ......... | A61F 9/008 351/205 |
| 6,183,086 B1 * | 2/2001 | Neubert | ............... | A61B 3/0008 351/221 |
| 6,789,900 B2 * | 9/2004 | Van de Velde | ......... | A61F 9/008 351/221 |
| 8,128,231 B2 * | 3/2012 | Smith | .................. | A61B 3/0008 351/212 |
| 8,480,233 B2 * | 7/2013 | Smith | .................. | A61B 3/0008 351/221 |

(Continued)

FOREIGN PATENT DOCUMENTS

WO    20111150431 A1    12/2011

OTHER PUBLICATIONS

Supplementary European Search Report, EP14762921, dated Oct. 28, 2016, 1 pge.

(Continued)

*Primary Examiner* — Eric S Gibson
(74) *Attorney, Agent, or Firm* — Innovation Counsel LLP (57) ABSTRACT

Apparatus and methods combine visible light output from two or more laser light sources emitting at different wavelengths to provide an illumination beam for illumination inside a human or animal body during a diagnostic or surgical procedure.

19 Claims, 5 Drawing Sheets

(56) References Cited

U.S. PATENT DOCUMENTS

| | | | |
|---|---|---|---|
| 8,662,670 B2* | 3/2014 | Papac | A61B 3/0008 128/898 |
| 2006/0055885 A1 | 3/2006 | Mizuno | |
| 2008/0246920 A1* | 10/2008 | Buczek | A61B 90/36 351/221 |
| 2009/0141238 A1* | 6/2009 | Asai | H04N 3/08 351/221 |
| 2009/0153797 A1* | 6/2009 | Allon | A61B 3/12 351/206 |
| 2009/0185251 A1 | 7/2009 | Chen et al. | |
| 2010/0177280 A1* | 7/2010 | Buczek | A61B 90/36 351/221 |
| 2010/0182569 A1* | 7/2010 | Artsyukhovich | A61B 1/0661 351/221 |
| 2010/0228089 A1* | 9/2010 | Hoffman | A61B 1/063 600/182 |
| 2011/0037948 A1* | 2/2011 | Horvath | A61B 1/0653 351/221 |
| 2011/0122366 A1* | 5/2011 | Smith | A61B 1/313 351/221 |
| 2011/0133101 A1 | 6/2011 | Viellerobe et al. | |
| 2011/0149246 A1* | 6/2011 | Artsyukhovich | A61B 3/0008 351/221 |
| 2011/0149247 A1* | 6/2011 | Artsyukhovich | A61B 3/0008 351/221 |
| 2011/0208004 A1 | 8/2011 | Feingold et al. | |
| 2011/0292343 A1* | 12/2011 | Papac | A61B 3/0008 351/221 |
| 2011/0299034 A1 | 12/2011 | Walsh et al. | |
| 2012/0041461 A1 | 2/2012 | McCollam | |
| 2012/0050684 A1* | 3/2012 | Smith | A61B 3/0008 351/221 |
| 2013/0038836 A1* | 2/2013 | Smith | A61B 3/0008 351/211 |
| 2014/0098342 A1* | 4/2014 | Webb | A61B 3/0008 351/206 |
| 2014/0128686 A1 | 5/2014 | Klaffenbach et al. | |
| 2015/0173606 A1* | 6/2015 | Yu | A61B 3/0008 351/206 |
| 2015/0366443 A1* | 12/2015 | Liolios | A61F 9/00821 600/249 |
| 2015/0366713 A1* | 12/2015 | Shazly | A61F 9/00821 606/5 |

OTHER PUBLICATIONS

Liolios et al., International Search Report corresponding to WO 2014/145465 AE, dated Sep. 18, 2014, 5 pages.

\* cited by examiner

EYE SAFE LASER ILLUMINATION IN OPHTHALMIC SURGERIES

CROSS REFERENCE TO RELATED APPLICATIONS

This application is a continuation of PCT Application No. PCT/US2014/030235 filed Mar. 17, 2014 and titled "Eye Safe Laser Illumination in Ophthalmic Surgeries", which claims benefit of priority to U.S. Provisional Patent Application No. 61/789,040 filed Mar. 15, 2013 and titled "Eye Safe Laser Illumination in Ophthalmic Surgeries", both of which are incorporated herein by reference in their entirety.

FIELD OF THE INVENTION

The invention relates generally to laser illumination in diagnostic and surgical procedures inside a human or animal body, and more particularly to laser illumination in ophthalmic diagnostic and surgical procedures.

BACKGROUND

Visualization of surgical targets in ophthalmic surgery is the cornerstone of multiple developments ongoing in the field. Visualization is a combination of the optics of the microscopes including safety filters as well as any lenses, the incoming light source including its instruments and fibers, and finally the optical target including any visualization dyes.

Illumination sources for ophthalmic surgery can be external or integrated into vitrectomy systems like, for example, the Alcon Constellation or the Bausch & Lomb Stellaris PC. The initial light sources for vitrectomy were metal halide or halogen bulbs. The output from these light sources was typically coupled into 20, 23, or 25 gauge-probes adapted for insertion into an eye to illuminate tissue to be treated during ophthalmic surgery.

The current trend in vitrectomy and vitreoretinal surgery is for smaller gauge instrumentation. Currently 23- or 25-gauge tools are the standard but the challenge to drive this to even smaller tools (27- and 29-gauge) is greatly limited by the illumination probes (using optical fibers) that provide the required illumination. Because they are extended incoherent sources, it is difficult to couple light from metal halide and halogen bulb light sources into the smaller diameter optical fibers of these narrower gauge probes. As a compromise, light may be coupled into a larger diameter optical fiber which is then tapered to a narrower gauge probe for insertion into an eye. This tapering also leads to light loss, however. Hence, as the trend to these smaller gauge instruments progresses, the halogen light sources that were previously used lose 50% of the brightness that they had provided with 20-gauge instrumentation.

To compensate for the light loss in the narrower gauge probes a new generation of light sources was developed based on brighter mercury vapor and xenon light bulbs. There is a concern however that the spectral distribution emitted by these light sources may cause retinal damage. To address this concern filters have been added to these illumination systems to block ultraviolet and blue light. These cut off filters typically start at 420 nm, but different designers have used cut offs at 435 nm, 475 nm, 485 nm, and even 515 nm.

Use of such filters typically changes the color of the viewing environment. Ophthalmic surgeons want clean illumination so they can view what the native tissue actually looks like. Yet, the more filtering of the blue light, the more yellow-looking the tissue will be. While white light emitted by these light sources is considered to provide "better" visualization of the tissue to be treated, the tradeoff is less time to safely perform the procedure. Further, the majority of the light output from mercury vapor light sources is centered on their two natural peaks at 550 nm and 580 nm. As a result the illumination is typically green-yellow.

The visualization and reliability of current light sources have additional limitations. The life of a xenon lamp is typically approximately 400 hours but it loses power throughout its useful lifetime. Most xenon bulbs don't reach their stable output until after ten minutes of "warm up". In addition, xenon and mercury vapor light sources are relatively inefficient and consequently heat up. As a result, cooling fans are typically required with these light sources.

SUMMARY

This specification discloses apparatus and methods in which visible light output from two or more laser light sources emitting at different wavelengths is combined to provide an illumination beam for illumination inside a human or animal body during a medical procedure.

In one aspect, an illumination device for use in an ophthalmic procedure comprises a housing, a blue diode laser positioned within the housing, a green diode laser positioned within the housing, a red diode laser positioned within the housing, an optical fiber connector attached to the housing, a lens, and beam combining and beam steering optical elements arranged to collinearly combine an output beam from the blue diode laser, an output beam from the green diode laser, and an output beam from the red diode laser to form an illumination beam and direct the illumination beam through the lens to focus into a core of an optical fiber illumination probe that may be externally attached to the optical fiber connector.

The illumination beam produces a speckle intensity pattern when delivered through the optical fiber illumination probe to illuminate internal eye tissue during the ophthalmic procedure. To reduce any distorting effect of the speckle pattern on observation of the illuminated tissue by a human observer, the illumination beam is incident on an optical element within the housing configured to oscillate at greater than or equal to about 30 Hertz over a distance or angular range sufficient to translate speckles in the speckle pattern by at least one speckle diameter. This blurs the speckles to smooth out the intensity pattern as observed by a human observer having normal visual response.

In another aspect, an illumination device for use in an ophthalmic procedure comprises a housing, a blue diode laser positioned within the housing, a green diode laser positioned within the housing, a red diode laser positioned within the housing, an optical fiber illumination probe having proximal and distal ends and externally connected at its proximal end to the housing, a lens, and beam combining and beam steering optical elements arranged to collinearly combine an output beam from the blue diode laser, an output beam from the green diode laser, and an output beam from the red diode laser to form an illumination beam and direct the illumination beam through the lens to focus into a core of the proximal end of the optical fiber illumination probe. The optical fiber illumination probe comprises an optical fiber having an untapered single diameter core and a needle-like sheath at its distal end. The needle-like sheath is adapted for insertion into an eye to illuminate internal eye tissue with the illumination beam.

In another aspect, a device for use in an ophthalmic procedure performed with an illumination laser beam and a green or yellow therapeutic laser beam comprises an illumination device and an optical filter. The illumination device includes a housing, a blue diode laser positioned within the housing, a green diode laser positioned within the housing, a red diode laser positioned within the housing, an optical fiber connector attached to the housing, a lens, and beam combining and beam steering optical elements arranged to collinearly combine an output beam from the blue diode laser, an output beam from the green diode laser, and an output beam from the red diode laser to form the illumination laser beam and direct the illumination laser beam through the lens to focus into a core of an optical fiber externally attached to the optical fiber connector. The optical filter has a transmittance less than or equal to about 0.1% for the therapeutic laser beam and a transmittance greater than or equal to about 85% for emission from the blue diode laser, emission from the green diode laser, and emission from the red diode laser.

These and other embodiments, features and advantages of the present invention will become more apparent to those skilled in the art when taken with reference to the following more detailed description of the invention in conjunction with the accompanying drawings that are first briefly described.

DETAILED DESCRIPTION

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used in this specification and the appended claims, the singular forms "a," "an," and "the" include plural referents unless the context clearly indicates otherwise.

This specification discloses apparatus and methods in which visible light output from two or more laser light sources emitting at different wavelengths is combined to provide an illumination beam for illumination inside a human or animal body during a diagnostic or surgical procedure. The output powers and/or the wavelengths of the illumination beam lasers may be selected and optionally varied to control the apparent color of the illumination beam. For example, the output powers and/or wavelengths of the illumination beams may be selected to provide an illumination beam that appears white, or a tinted white, to a human eye having normal vision. Further, the output powers and or wavelengths may be selected to provide a white illumination beam having a desired particular color temperature. Optionally, the output power of each laser may be controlled by a user to adjust the apparent color of the illumination beam.

Apparatus (such as illumination device 10 described below) may be configured with one or more pre-set options providing illumination beams of particular pre-set apparent colors. Upon a user selecting such a pre-set option, the illumination device will operate the two or more illumination beam lasers at appropriate wavelengths and/or appropriate relative powers to provide an illumination beam of the corresponding apparent color. Such apparatus may be similarly configured to provide an illumination beam at the selected color at one or more pre-set power levels.

The illumination beam may be used in combination with a therapeutic laser beam to illuminate tissue to be treated with the therapeutic laser beam. The wavelength of the therapeutic laser beam typically differs from the wavelengths of all of the laser light sources used to form the illumination beam. For example, as described in more detail below the wavelength of the therapeutic laser beam may differ by at least about 5 nm, at least about 8 nm, or at least about 10 nm from the wavelengths of the laser light sources from which the illumination beam is formed.

The differences between the wavelength of the therapeutic laser beam and the wavelengths of the laser light sources used to form the illumination beam facilitate use of an optical filter to protect an observer from the therapeutic laser beam while still allowing the observer to observe the tissue with all spectral components of the illumination beam. For example, the optical filter may have high transmittance at the wavelengths of the laser light sources used to form the illumination beam, and low transmittance at the wavelength of the therapeutic beam.

The use of visible light lasers having different wavelengths to provide an (e.g., white) illumination beam may provide numerous benefits compared to the currently implemented solutions. First, because lasers provide monochromatic light, they can be more energy efficient. Additionally, because the light is emitted from a small source and is collimated or relatively easily collimated, it may be easily coupled into a small diameter optical fiber core and transmitted through the optical fiber for use illuminating the tissue to be treated. This may allow further miniaturization of diagnostic and surgical instruments.

As further described below, the output powers of the lasers forming the illumination beam and/or the divergence cone angle of the illumination beam as it exits an optical fiber probe may be selected so that the illumination beam is eye-safe for all personnel present in the operating room. As an additional safety precaution, the power of the illumination beam may be monitored and the illumination beam may be mechanically or electronically interrupted if the power rises to or above some predetermined threshold corresponding to risk to the patient or to other personnel present.

The figures and detailed description below are directed to apparatus and methods in which visible light output from two or more laser light sources emitting at different wavelengths is combined to provide an illumination beam for ophthalmic diagnostic and/or surgical procedures. However, the apparatus and methods described herein, and suitable variations, may also be used for example in endoscopic procedures to illuminate internal portions of the colon or of the esophagus, in coronary diagnostic and surgical procedures performed using catheters, in other minimally invasive procedures employing catheters, and in any other suitable medical procedure.

Figure 1A:
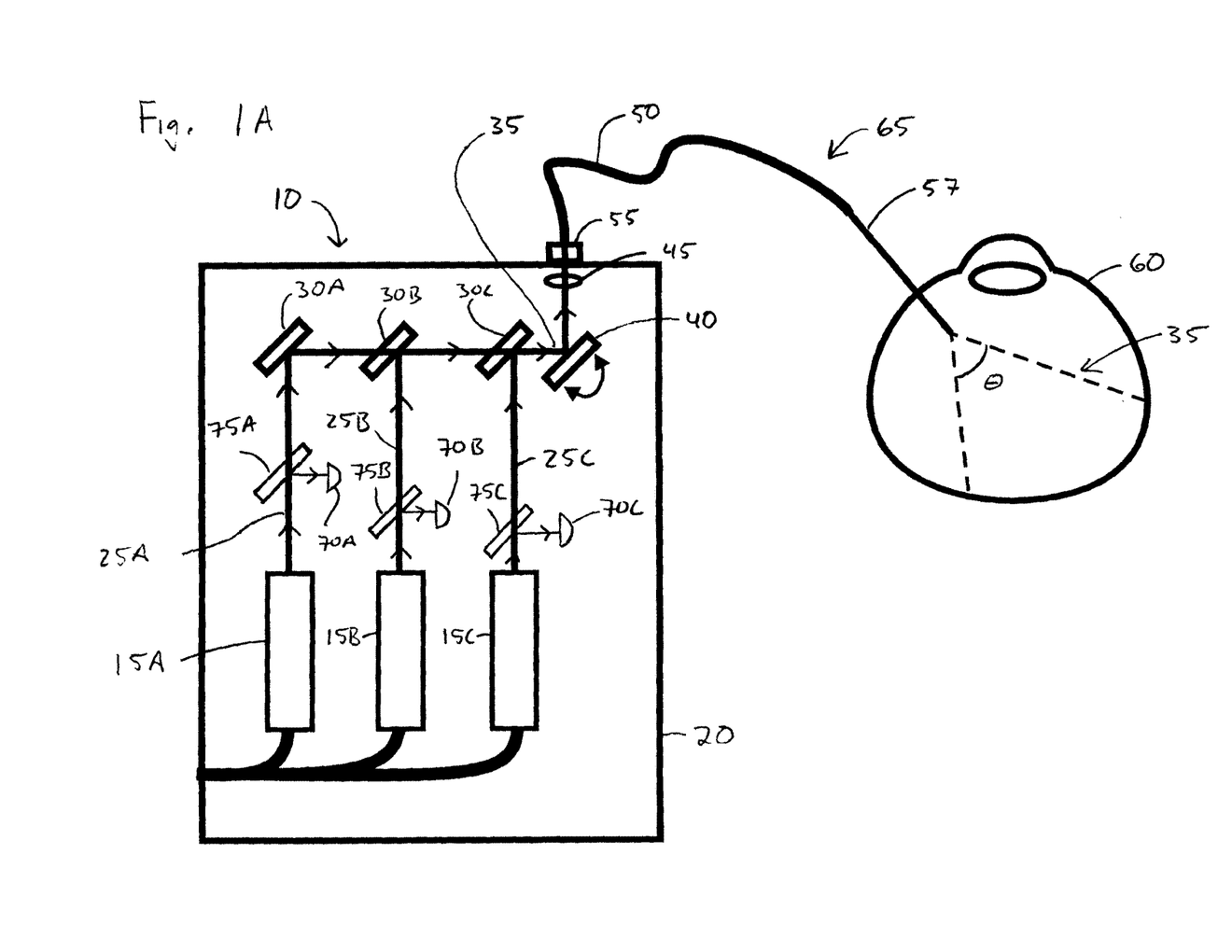
FIG. 1A shows an example laser illumination device optically coupled to an optical fiber probe inserted into an eye to provide illumination for an ophthalmic procedure.

Referring now to FIG. 1A, an example illumination device 10 comprises three visible light lasers 15A-15C optionally disposed within a housing 20. Light beams 25A-25C emitted by these lasers are combined collinearly by beam steering optical elements 30A-30C to form illumination beam 35 incident on an optical element 40, which directs beam 35 through a lens 45 that focuses beam 35 into the core portion of optical fiber 50. One end of optical fiber 50 is attached to illumination device 10 with connector 55, through which illumination beam 35 is coupled into the optical fiber. At least the core of the other end of optical fiber 50 is sheathed by a needle-like sheath 57 adapted for insertion into an eye 60. Sheath 57 may be formed from metal, for example. Optical fiber 50 and sheath 55 together form an optical fiber probe 65. (Similarly constructed optical fiber probes may be used in other surgical and diagnostic applications of the illumination methods and devices described herein). Illumination beam 35 is emitted from the end of optical fiber probe 65 with a cone angle θ to illuminate internal portions of the eye.

Lasers 15A-15C may be semiconductor diode lasers, for example. Typically, one laser emits in the blue region of the visible spectrum (e.g., about 400 nm to about 480 nm), another emits in the green region of the visible spectrum (e.g., about 500 nm to about 570 nm), and the third emits in the red region of the visible spectrum (e.g., about 620 nm to about 700 nm), so that in combination the output of the three lasers may form an apparently white illumination beam 35.

Typically, lasers 15A-15C each emit in a narrow band around a center wavelength. The blue laser emission may have a center wavelength greater than or equal to about 440 nm, or about 450 nm, for example. The green laser emission may have a center wavelength of about 515 nm, or about 520 nm, or about 550 nm, for example. The red laser emission may have a center wavelength of about 635 nm or about 640 nm, for example. To achieve a large dynamic range of available apparent color it may be important to have good separation between the illumination source wavelengths, with each source in the visible spectrum 400 nm to 700 nm, or in the highly visible spectrum 450 nm to 640 nm range.

Figure 1B:
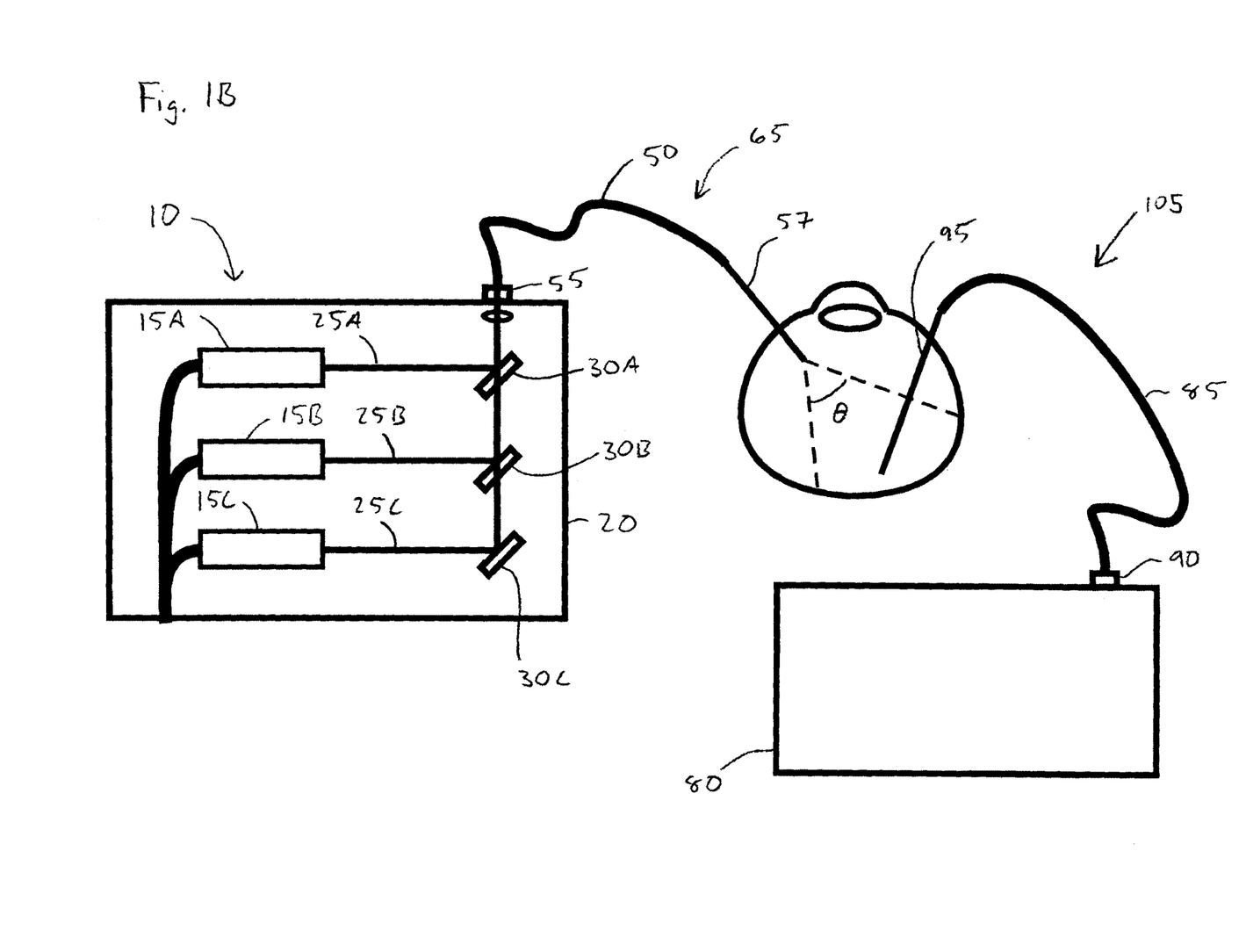
FIG. 1B shows the device of FIG. 1A, and in addition shows a therapeutic laser light source optically coupled to another optical fiber probe inserted into the eye to provide a therapeutic beam with which an ophthalmic surgical procedure may be performed.
Figure 1C:
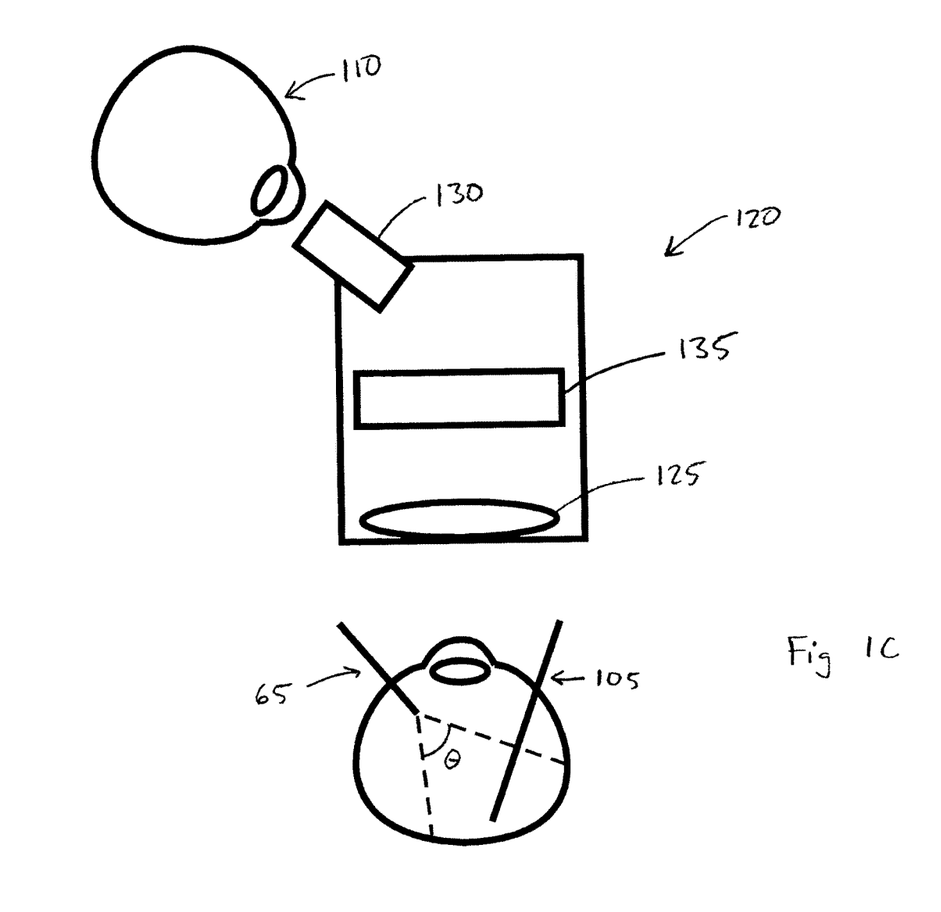
FIG. 1C shows optical fiber probes inserted into the eye, as in FIG. 1B, and in addition shows a microscope through which the ophthalmic procedure may be observed. The microscope includes an optical filter with a low transmittance at the therapeutic laser beam wavelengths and a high transmittance for the wavelengths emitted by the laser illumination device.

Although FIGS. 1A-1C show illumination device 10 comprising three lasers, any suitable number of lasers (e.g., two or more than three) may be used to form illumination beam 35. The lasers may emit in any suitable regions of the visible spectrum.

If illumination device 10 is intended for use in a diagnostic or surgical procedure performed with a therapeutic laser beam, lasers 15A-15C may be selected to emit at center wavelengths different from the center wavelength of the therapeutic laser beam. For example, the center wavelengths of lasers 15A-15C may each be a wavelength different from 532 nm, 561 nm, and/or 577 nm (i.e., typical commercially available ophthalmic therapeutic laser wavelengths). The center wavelengths of lasers 15A-15C may differ from the center wavelength of the therapeutic laser by, for example, at least about 5 nm, at least about 8 nm, or at least about 10 nm.

As described in more detail below, using lasers 15A-15C having center wavelengths differing from the center wavelength of the therapeutic laser beam allows use of an optical filter to protect an observer's eye from the therapeutic laser beam while allowing the observer to see all or substantially all spectral components of the illumination beam.

Referring again to FIG. 1A, optionally the output power of each of lasers 15A-15C may be monitored with photodetectors 70A-70C to which portions of beams 25A-25C are directed, respectively, by beam splitters 75A-75C. Any suitable photo-detectors and beam splitters may be used for this function. Also optionally, lasers 15A-15C may be individually controlled to adjust their output power, thereby controlling their relative contributions to illumination beam 35 and thus controlling the spectrum and apparent color of illumination beam 35. This may be accomplished for example by individually controlling electric power supplied to each laser while monitoring the individual laser output powers. The lasers may each be actively controlled to provide substantially constant power at desired power levels. The total power of illumination beam 35 may be separately measured with another beam splitter and photo-detector (not shown) sampling the illumination beam, for example, or determined from separate measurements of the power in laser beams 25A-25C. The power in each of laser beams 25A-25C may be maintained at levels, for example, greater than or equal to about 1 mW. The power in each of laser beams 25A-25C may be maintained at levels, for example, less than or equal to about 30 mW. The total power of the illumination beam may be maintained, for example, at less than or equal to about 30 mW.

Beam steering optical elements 30A-30C and optical element 40 may be or comprise, for example, any suitable refractive, diffractive, reflective, or partially reflective (e.g., beam splitting) optical elements arranged in any suitable manner to combine laser beams 25A-25C to form illumination beam 35 and direct it through lens 45 into the core of optical fiber 50. Optical element 40 may be absent, for example.

Lens 45 may be any suitable lens. Lens 45 may focus beam 35 to a diameter at the input face of optical fiber 50 less than or equal to the diameter of the core portion of optical fiber 50. In addition, or alternatively, lens 45 may focus beam 35 to a cone angle corresponding to a numerical aperture (NA) less than or approximately matching the NA of the optical fiber core.

The coherent laser light of illumination beam 35 emitted from the end of optical fiber probe 65 may produce a speckle intensity pattern on the tissue it illuminates. Such speckle intensity patterns result from the interference of many waves of the same frequency, having different phases and amplitudes, which add together to give a resultant wave whose amplitude, and therefore intensity, varies randomly.

An observer of tissue illuminated by such a speckle pattern may have a distorted and possibly confusing view of the tissue, which might compromise the diagnostic or surgical procedure. To address this issue, in some variations the direction of beam 35 is altered repetitively (e.g., in an oscillating manner) over a small angular range at a frequency of about 30 Hertz or greater prior to beam 35 being coupled into optical fiber 50. As a result, the speckles in the speckle pattern move in a corresponding manner across the illuminated tissue. Typically, the magnitude of the small changes made to the direction of beam 35 is selected to be small enough so that the power in beam 35 coupled into optical fiber 50 is not significantly reduced, but large enough so that speckles in the speckle pattern move across the tissue a distance of at least one speckle diameter. Beam 35 typically moves by only a fraction of a beam diameter. If the beam direction changes were performed sufficiently slowly, the motion of the speckles would be observable by a human eye. However, if the beam direction changes are performed at about 30 Hertz or greater (as taught here) the speckles will appear to a human observer to be smeared out into a smoother intensity pattern that does not significantly distort the observer's view of the tissue.

Such repetitive small changes in the direction of beam 35 may be produced, for example, by reflecting beam 35 from, or transmitting it through, a moving or vibrating optical element. The optical element may be or comprise, for example, a mirror galvanometer. Alternatively, the optical element may be or comprise, for example, a reflective optical element translated by piezo actuators. For example, piezo actuators may be glued into a kinematic mount between the back plate of the reflective optical element and the wobble plate in place of the usual adjustment screws. As yet another alternative, beam 35 may be transmitted through a spinning prism. If beam 35 has an elliptical transverse profile and is scanned in only one direction to smooth out the speckles, if may be preferable to align the scan direction with the minor axis of the laser beam profile. In the example of FIG. 1A, reflective optical element 40 is moved in an oscillating manner, as indicated by the arrows, to smooth out the speckle pattern as just described.

Dithering or otherwise repetitively altering the direction of beam 35 to smooth out the speckle pattern may be desirable but is not required.

Referring again to FIG. 1A, optical fiber 50 typically has a constant (untapered) core diameter of less than or equal to about 200 microns, less than or equal to about 100 microns, or less than or equal to about 50 microns. In particular, because illumination beam 35 is a laser beam that may be efficiently coupled into a small diameter optical fiber core, it is not necessary to use a tapered fiber having a large core at an input end into which illumination light is coupled and a narrower core portion at an output end through which light is emitted to illuminate tissue. Optical fiber 50 may have an external diameter less than or equal to about 200 microns, for example, allowing it to fit within conventional irrigation probes for example, and/or to fit within the internal diameter of a standard 23 gauge needle. Optical fiber 50 typically has a numerical aperture greater than or equal to about 0.22, or greater than or equal to about 0.4, or greater than or equal to about 0.45, or greater than or equal to about 0.5. Illumination beam 35 may be emitted from the output end of optical fiber probe 65 with a full width at half maximum divergence angle $\theta$ of greater than or equal to about 80 degrees in air (half angle greater than or equal to about 40 degrees in air), for example. Illumination beam 35 may be emitted from the output end of optical fiber probe 65 with a full width at half maximum divergence angle $\theta$ of greater than or equal to about 60 degrees in water (half angle greater than or equal to about 30 degrees in water), for example. Needle-like sheath 57 may be, for example, about 20 to about 25 gauge.

Typically the output powers of the lasers forming the illumination beam and/or the divergence cone angle of the illumination beam as it exits the optical fiber probe are selected so that the illumination beam is eye-safe for all personnel present in the operating room having a normal blink reflex. For example, the total output power and divergence of illumination beam output from optical fiber probe 65 may be selected so that less than or equal to about 1 mW is transmitted through a 7 mm circular aperture located at a distance of about 70 mm from the output end of the probe and at the center of the maximum of the illumination distribution. In addition, a shutter may be positioned in the path of illumination beam 35 to prevent beam 35 from exiting housing 20 through connector 55 if illumination device 10 is not connected to an optical fiber probe.

Referring now to FIG. 1B, as noted above illumination device 10 and optical fiber probe 65 may be used in combination with a therapeutic laser beam. In the illustrated example, a therapeutic laser beam provided by therapeutic laser source 80 is coupled into a therapeutic optical fiber probe 105 through a connector 90. Optical fiber probe 105 comprises an optical fiber 85, connected to the therapeutic laser beam source, and a needle-like sheath 95 that may be inserted into an eye (or other tissue) to deliver the therapeutic laser beam to the tissue to be treated. The therapeutic laser beam may have a wavelength of about 532 nm, for example, which is conventional for retinal photocoagulation surgeries. Alternatively, the therapeutic laser beam may have a wavelength of about 561 nm, or about 577 nm, or any other suitable wavelength. The therapeutic laser beam is typically output from the end of optical fiber probe 105 at a power of greater than or equal to about 100 mW. The therapeutic laser beam is typically emitted from the end of optical fiber probe 105 with a full width at half maximum divergence angle of greater than or equal to about 25 degrees in air, for example.

Referring now to FIG. 1C, an observer 110 (shown as an eye) may use a microscope 120 to observe a surgical procedure in an eye performed using a therapeutic laser beam delivered through optical fiber probe 105 under illumination with an illumination beam delivered through optical fiber probe 65. In the illustrated example, microscope 120 includes a conventional objective lens 125 and a conventional eyepiece 130. In addition, microscope 120 includes an optical filter 135 configured to block transmission of light from the therapeutic laser beam while passing all or substantially all spectral components of the illumination beam. For example, the filter may have a transmittance less than or equal to about 0.1%, or less than or equal to about 0.01% for all spectral components of the therapeutic laser beam, and a transmittance greater than or equal to about 75%, or greater than or equal to about 85%, or greater than or equal to about 90%, or greater than or equal to about 95%, or greater than or equal to about 98% for all spectral components of the illumination beam.

Filter 135 may be moveable into and out of the observer's line of sight in the microscope, as desired. For example, the filter may be out of the observer's line of sight until the observer utilizes the therapeutic laser, at which point the filter may be (e.g. automatically) moved into the line of sight position. In some variations, the transition between filter in and filter out does not noticeably change the intensity, saturation and hue of the observed illuminated field of view.

Typically, filter 135 has a stop band centered at about the wavelength of the therapeutic laser beam. The stop band has a width of less than or equal to about 5 nm, or less than or equal to about 10 nm, or less than or equal to about 15 nm in which transmittance is less than or equal to about 0.1%, or less than or equal to about 0.01%. In addition, filter 135 has a pass band on the blue side of the stop band with a transmittance of greater than or equal to about 75%, or greater than or equal to about 85%, or greater than or equal to about 90%, or greater than or equal to about 95%, or greater than or equal to about 98% for blue, or blue and green components of illumination beam 35. Filter 135 also has a pass band on the red side of the stop band with a transmittance of greater than or equal to about 75%, or greater than or equal to about 85%, or greater than or equal to about 90%, or greater than or equal to about 95%, or greater than or equal to about 98% for red, or red and green components of illumination beam 35.

An important feature of filter 135 is that it has a high transmittance for all spectral components of the illumination beam, including those with wavelengths close to the wavelength of the therapeutic laser beam. For example, filter 135 may have a high transmittance (greater than or equal to about 75%, or greater than or equal to about 85%, or greater than or equal to about 90%, or greater than or equal to about 95%, or greater than or equal to about 98%) for a component of the illumination beam at about 515 nm, or about 520 nm, or about 550 nm while having a low transmittance (less than or equal to about 0.1%, or less than or equal to about 0.01%.) for a therapeutic laser beam at about 532 nm.

Figure 2:
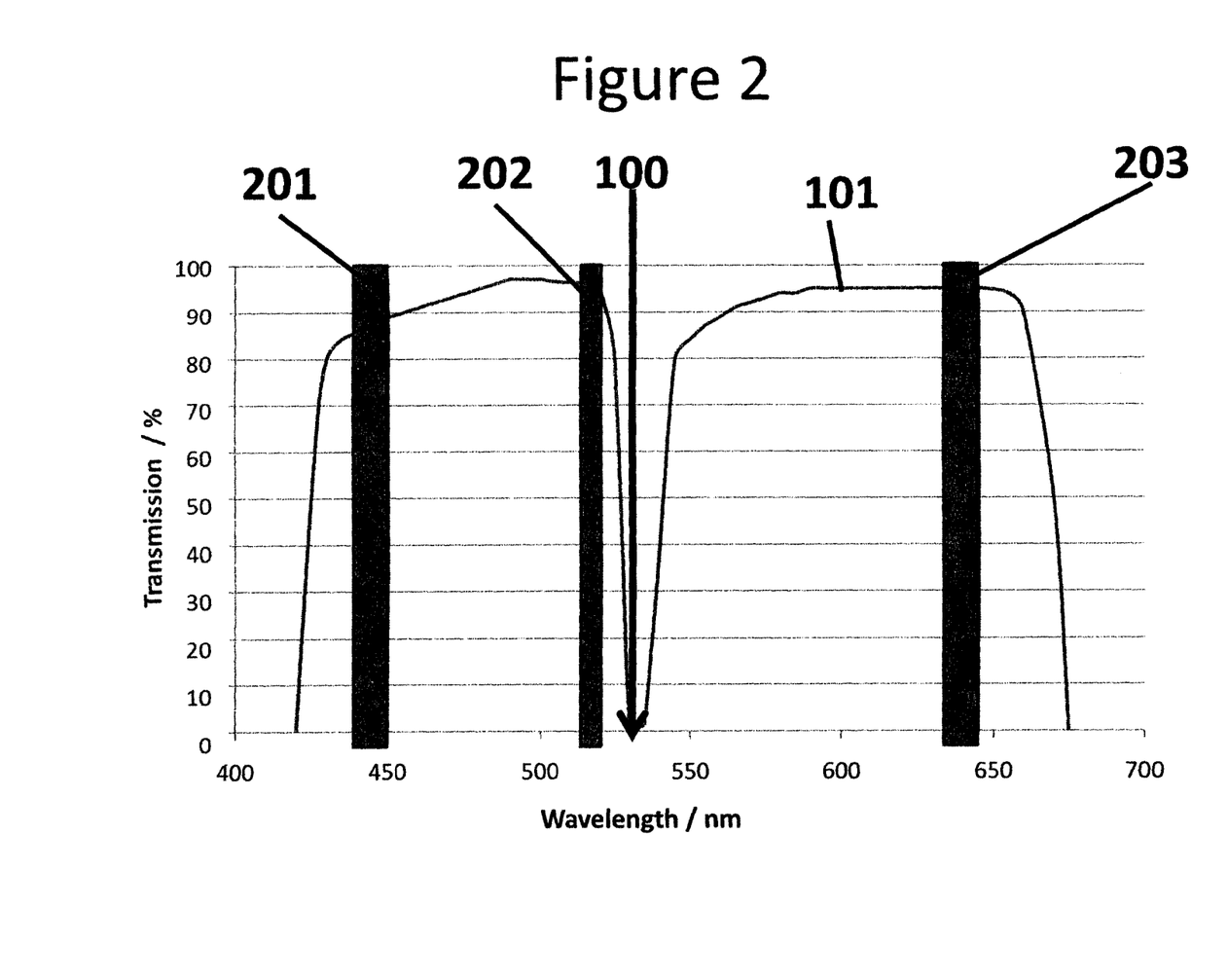
FIG. 2 shows an example transmission spectrum of the optical filter of FIG. 1C. This example filter may be used in ophthalmic or other laser surgery to protect an observer from the therapeutic laser beam while allowing illumination of the treated tissue with an illumination beam appearing white, or a tinted white, to a human observer having normal color vision. This figure also shows the wavelength of the therapeutic beam, and the center wavelengths of three narrow band visible laser beams combined to form the illumination beam, that may be used effectively with this filter.

FIG. 2 shows a transmission spectrum 101 for an example optical filter 135 that may be used with a therapeutic laser beam at about 532 nm and an illumination beam formed from a combination of three laser beams having emission centered at about 450 nm, about 515 nm, and about 635 nm. The therapeutic laser wavelength is indicated by reference numeral 100, and the emission wavelengths of the lasers contributing to the illumination beam are indicated by reference numerals 201, 202, and 203. In this example the stop band has a transmittance less than or equal to about 0.01% between about 529 nm and about 535 nm, blocking the 532 nm therapeutic laser beam, and has a transmittance of greater than or equal to about 90% for the green component of the illumination beam at about 515 nm.

Figure 3:
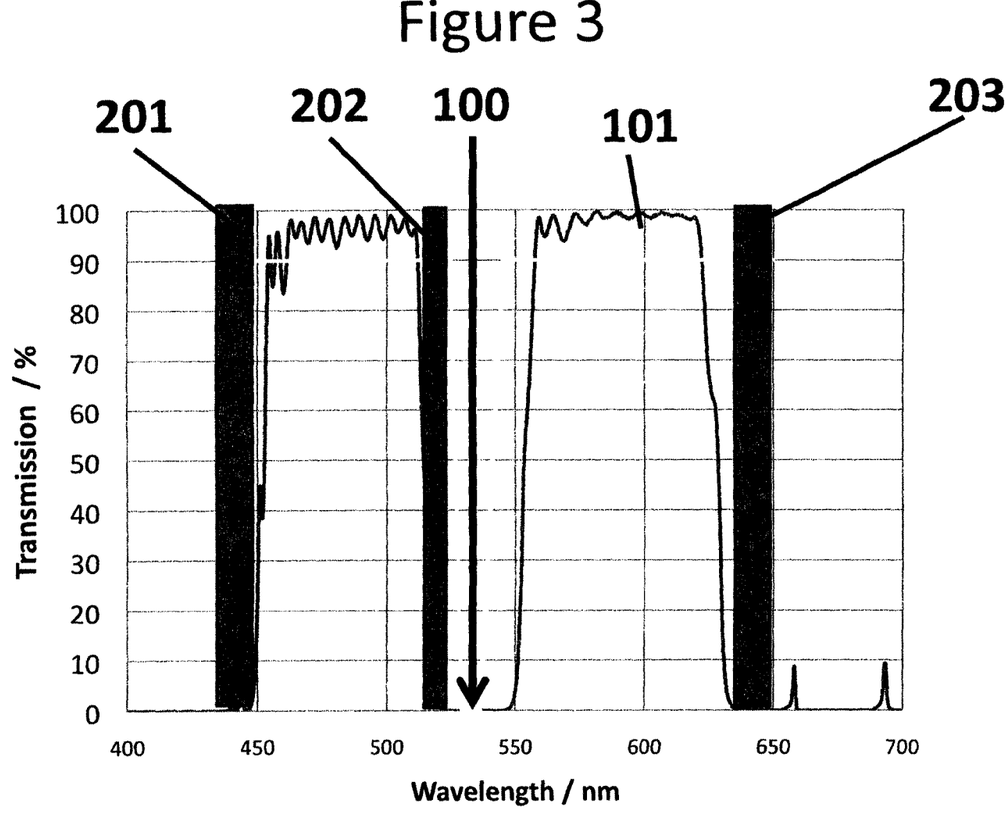
FIG. 3 shows a transmission spectrum of an optical filter that would likely not perform satisfactorily, compared to the filter of FIG. 2, in combination with the therapeutic and illumination beam wavelengths shown in FIG. 2.

FIG. 3 shows a transmission spectrum of an example optical filter that would not perform as satisfactorily, compared to the filter of FIG. 2, in combination with the therapeutic and illumination beam wavelengths shown in FIG. 2. In particular, in this example the stop band is sufficiently wide to significantly reduce the transmittance for the green component of the illumination beam at about 515 nm. As a consequence, the green component would not strongly contribute to the illumination observed by the observer. The red and blue components of the illumination beam would dominate, and the observed illumination would be biased toward magenta.

This disclosure is illustrative and not limiting. Further modifications will be apparent to one skilled in the art in light of this disclosure and are intended to fall within the scope of the appended claims.

What is claimed is:

1. An illumination device for use in an ophthalmic procedure, the illumination device comprising:
    a housing;
    a blue diode laser positioned within the housing;
    a green diode laser positioned within the housing;
    a red diode laser positioned within the housing;
    an optical fiber illumination probe having proximal and distal ends and externally connected at its proximal end to the housing;
    a lens; and
    beam combining and beam steering optical elements arranged to collinearly combine an output beam from the blue diode laser, an output beam from the green diode laser, and an output beam from the red diode laser to form an illumination beam and direct the illumination beam through the lens to focus into a core of the proximal end of the optical fiber illumination probe;
    wherein the optical fiber illumination probe comprises a needle-like sheath at its distal end and an optical fiber having an untapered single diameter core extending from the proximal end of the optical fiber illumination probe to the needle-like sheath, the needle-like sheath adapted for insertion into an eye to illuminate internal eye tissue with the illumination beam; and
    wherein the illumination beam has a maximum power and divergence as it exits the optical fiber illumination probe such that less than or equal to 1 mW is transmitted through a 7 mm circular aperture located at a distance of 70 mm from the distal end of the optical fiber illumination probe and centered on a spatial maximum of the illumination beam.

2. The illumination device of claim 1, wherein the illumination beam is perceived as white or a tinted white to a human having normal color vision.

3. The illumination device of claim 1, wherein output powers of the blue diode laser, the green diode laser, and the red diode laser are independently monitored and controllable by a user to select an apparent color and total power of the illumination beam.

4. The illumination device of claim 1, wherein the optical fiber core has a diameter less than or equal to 200 microns.

5. The illumination device of claim 1, wherein the optical fiber core has a diameter less than or equal to 100 microns.

6. The illumination device of claim 1, wherein the optical fiber core has a diameter less than or equal to 50 microns.

7. The illumination device of claim 1, wherein the optical fiber has a numerical aperture greater than or equal to 0.22.

8. The illumination device of claim 1, wherein the optical fiber has a numerical aperture greater than or equal to 0.45.

9. The illumination device of claim 1, wherein the needle-like sheath has a diameter smaller than 20 gauge.

10. The illumination device of claim 1, wherein the blue diode laser beam, the green diode laser beam, and the red diode laser beam all have center wavelengths differing from 532 nm, 561 nm, and 577 nm by at least 8 nm.

11. The illumination device of claim 1, comprising an optical filter having a transmittance at 532 nm less than or equal to 0.1% and a transmittance greater than or equal to 85% for emission from the blue diode laser, emission from the green diode laser, and emission from the red diode laser.

12. The illumination device of claim 11, wherein the green diode laser emission is centered at 515 nm.

13. The illumination device of claim 11, wherein the green diode laser emission is centered at 550 nm.

14. The illumination device of claim 1, comprising an optical filter having a transmittance at 561 nm less than or equal to 0.1% and a transmittance greater than or equal to 85% for emission from the blue diode laser, emission from the green diode laser, and emission from the red diode laser.

15. The illumination device of claim 14, wherein the green diode laser emission is centered at 515 nm.

16. The illumination device of claim 14, wherein the green diode laser emission is centered at 550 nm.

17. The illumination device of claim 1, comprising an optical filter having a transmittance at 577 nm less than or equal to 0.1% and a transmittance greater than or equal to 85% for emission from the blue diode laser, emission from the green diode laser, and emission from the red diode laser.

18. The illumination device of claim 17, wherein the green diode laser emission is centered at 515 nm.

19. The illumination device of claim 17, wherein the green diode laser emission is centered at 550 nm.

* * * * *